United States Patent [19]
Simon

[11] Patent Number: 4,790,329
[45] Date of Patent: Dec. 13, 1988

[54] ADJUSTABLE BIOPSY LOCALIZATION DEVICE

[75] Inventor: Morris Simon, Boston, Mass.

[73] Assignee: Trustees of Beth Israel Hospital, Boston, Mass.

[21] Appl. No.: 62,443

[22] Filed: Jun. 12, 1987

[51] Int. Cl.⁴ .............................................. A61B 10/00
[52] U.S. Cl. ..................................... 128/749; 128/754
[58] Field of Search ............... 128/749, 751, 754, 763, 128/310; 604/57, 59, 60, 164, 165; 403/329, 377, 378

[56] References Cited
U.S. PATENT DOCUMENTS 860,270 7/1907 Trewhella ........................... 403/329
3,039,468 6/1962 Price ................................... 604/164
4,345,606 8/1982 Littleford ............................ 604/165

Primary Examiner—Edward M. Coven
Assistant Examiner—Randy Citrin
Attorney, Agent, or Firm—David Prashker

[57] ABSTRACT

A unique adjustable biopsy localization device is provided which allows for insertion at a selected anatomic site, visualized radiologically, and which can be secured in an engaged position, disengaged into a moveable position and repositioned at will. The localization device comprises cannula and rod elements as a preassembled unit which can be sterilized, packaged and conveniently stored until required for use by the radiologist or surgeon.

7 Claims, 6 Drawing Sheets

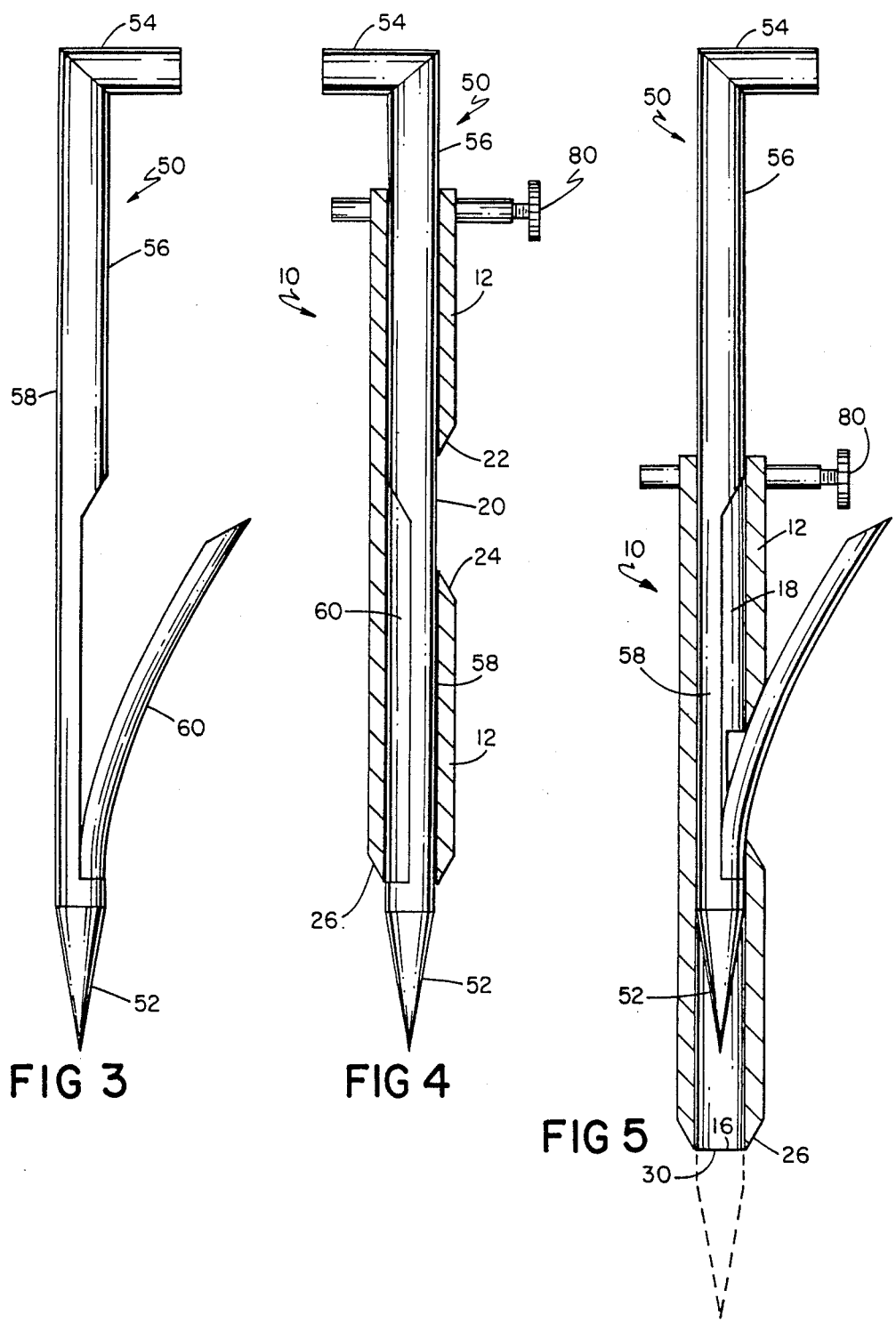

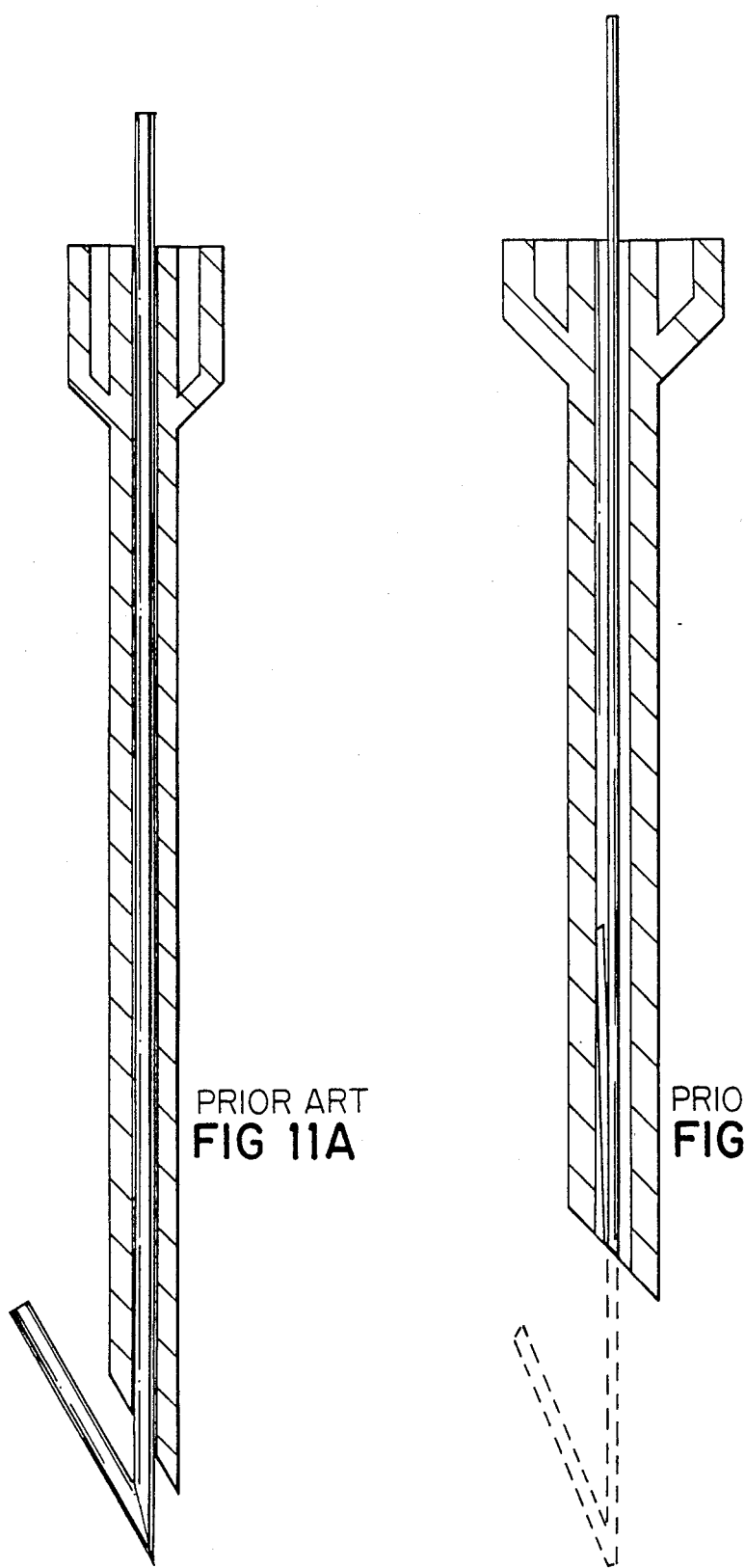

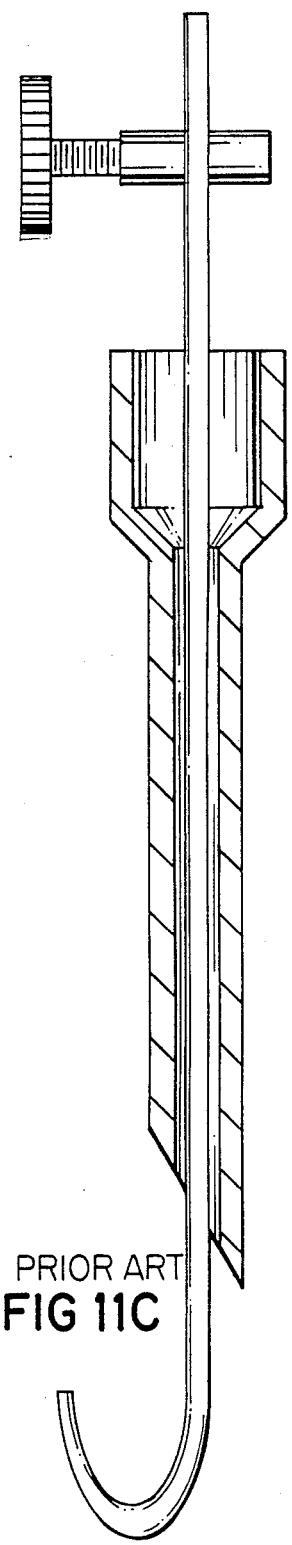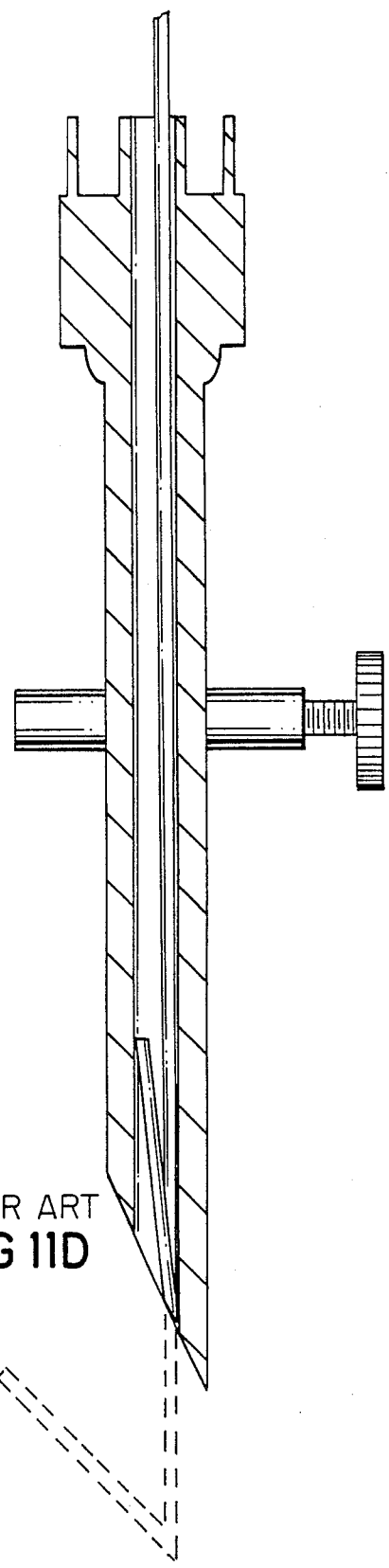
PRIOR ART
FIG 11C
PRIOR ART
FIG 11D

ADJUSTABLE BIOPSY LOCALIZATION DEVICE

FIELD OF THE INVENTION

The present invention is concerned with guiding instruments and devices used by physicians and surgeons to localize specific anatomic sites or diseased tissues in the body for biopsy examination.

BACKGROUND OF THE INVENTION

Currently available radiologic imaging techniques makes it possible to display a localized focus of disease deep within specific organs or tissues of the body. A typical example is the visualization of a small cancerous mass in the breast of a woman. In order to accurately diagnose and effectively treat the disease, the mass in the breast, it may be necessary for a surgeon to excise a portion of the diseased tissue for microscopic examination and analysis. A recurrent problem for the physician and surgeon is that even with the help of X-ray films, the surgical search for a small lesion or mass often proves extremely difficult; can cause considerable damage to the normal tissues surrounding the lesion; and often fails in the attempt.

In recent years the surgery, commonly termed a biopsy procedure, has been greatly simplified by the radiologist placing a long, wire marker having a small hook or spur at one end into the tissue, under radiological control. Once the wire hook has been inserted at the chosen site, films are taken to document the exact relationship of the wire to the target lesion. The wire length serves as a marker and guides the surgeon to the suspected lesion or mass. Presuming that the wire guide has been accurately positioned, the biopsy can be performed rapidly and accurately. Unfortunately, if the wire guide is shown by radiological examination, to be improperly situated, one or more additional hooked wires must be inserted into the tissue and subsequently verified radiologically as being in the proper localized site. Once inserted, accurately or inaccurately, it is usually the surgeon who will remove the wire markers at the time of biopsy because the hooked end of the wire is embedded in the tissues and cannot be easily withdrawn without tearing the surrounding tissues.

A variety of different wire guides and needle devices have been developed to aid the surgeon in the biopsy procedure and are in routine use today. These conventionally available wire guide devices are of four general types: the Frank localizer; the Kopans locater; the Homer needle/wire localizer; and the Sadowsky needle marking system. Each of these will be described individually in detail.

The Frank localizer is illustrated in cross-sectional view by prior art FIG. 11A and typically consists of a 12 centimeter (hereinafter "cm") wire with a 5 millimeter (hereinafter "mm") hook or spur at the tissue insertion end. The hooked wire is typically carried by a 20 gauge syringe needle having about a 9 cm length. While the length of the wire is inserted into the bore of the syringe needle, the hook remains outside the needle tip during its introduction into the body tissue at the preselected site of insertion. Unfortunately, once the wire and needle has been inserted at the chosen site, the needle can only be advanced deeper into the tissue; it cannot be withdrawn even slightly without releasing the wire into the tissues. The wire itself cannot be repositioned at any time, even if it is not situated close enough to the target lesion. Furthermore, the wire is extremely thin, difficult to palpate, and may be accidentally cut during the surgery.

The Kopans locater is illustrated in cross-sectional view by prior art FIG. 11B. As designed, the wire length and hooked end are intended to remain within the bore of the needle during insertion into the tissues. Once positioned, the beveled needle tip is checked radiologically for proximity to the target area; if incorrectly situated, the needle can be adjusted if necessary. Once believed to be in the correct target area, the wire hook within the bore of the needle is extended and thereby released into the surrounding tissue. The hollow needle is then typically removed leaving the hooked wire in the extended position within the tissue. There are, however, some flaws in the Kopans system. The tip of the needle is not completely secure in the tissue after insertion and prior to release of the wire hook; it may become displaced by involuntary movement of the subject between the time the needle position is radiologically checked and the wire hook is finally extended. Also, the entire wire length may be drawn into the tissues during the position verification procedure; accordingly either the tissue, such as a breast, must be kept in constant compression or an external screw-clamp must be utilized to prevent the length of the wire from being drawn into the tissues and lost. The wire within the needle bore typically has a thickened segment along its length to assist surgical palpatation, but may become broken or accidentally cut above or below this. Since the needle lumen must accommodate both the hook and the shaft of the wire, the wire diameter can be no more than half the diameter of the lumen, or one quarter of its cross-sectional area. This necessitates a larger bore needle for any required wire thickness.

The Homer needle/wire localizer is illustrated in cross-sectional view by prior art FIG. 11C. Typically, the device comes in either long or short length formats. A beveled syringe needle is utilized into which is inserted a J-shaped wire formed from a metal with strong spring recovery which can be temporarily straightened as it is drawn into the bore of the needle. Typically, a wire screw-clamp is attached to the wire at its proximal end to indicate the orientation of the J-shaped hook and to provide some indication of the depth of wire in the needle and tissues. During insertion of the needle into the tissues, the J-shaped hook remains within the bore of the needle. Once the tip of the needle is found to be in the desired area of the target lesion, the wire is extended through the needle bore and the J-shaped hook pushes out into the surrounding tissue in a sweeping curve. The needle is optionally left in place within the tissue along with the wire during the biopsy. The needle, however, is difficult to control during insertion such that the J-shaped hook may be delivered at an unintended location. It is very easy to overextend past the target area and equally common to extend at an inappropriate angle because of the J-shaped hook configuration. Furthermore, withdrawing the needle can result in a cutting sweep of tissue by the J-shaped hook as it is retracted into the bore of the needle. Finally, while the clamp at the proximal end of the wire is meant to indicate the orientation of the J-shaped hook, it is common for the wire to become twisted or disoriented with relation to the screw-clamp.

The Sadowsky marking system is illustrated in cross-sectional view by prior art FIG. 11D. The Sadowsky needle and wire guide is similar to the Kopans device previously described herein. A hooked wire is intended to remain within the bore of the beveled edge needle during insertion of the device into the tissue. A screw clamp is typically mounted on the outside of the needle to a preset needle depth believed to be appropriate for the target lesion. The wire also usually has individual markings along its length to identify its depth as well. Once the needle has been inserted into the tissue and been verified as to correct positioning, the hooked wire is advanced out of the needle bore into the tissue substantially as shown. Once advanced into the tissue, the hooked wire cannot be withdrawn or repositioned. The other deficiencies of the Sadowsky system are similar to those enumerated for the Kopans system previously.

Clearly, there is a recognized and continuing need for a biopsy guide device which is adjustable, removable without destruction of localized tissue, and can be repositioned if necessary without need for either additional guide devices or further damage to the patient. The availability of such an adjustable biopsy guide would be recognized and acknowledged by physicians and surgeons alike as being a valuable advance in this art.

SUMMARY OF THE INVENTION

The present invention provides an adjustable biopsy localization device comprising a cannula having a substantially cylindrical tubular wall and an internal lumen; an open slot in the tubular wall; and a pointed rod inserted into and passing through the lumen of the cannula, the rod being partially split along its length to provide a barb-like appendage extendable through the slot in the tubular wall.

The biopsy localization device may be inserted and removed at will without major injury to the tissues of the subject; may be engaged and secured into a specific localized site for radiological verification of position and then disengaged if desired for repositioning at will; may be entirely removed from the first positional site and reinserted at a new position as often as necessary until the target lesion is reached; and cannot be broken, be cut, or become lost within the internal tissues of the subject.

DETAILED DESCRIPTION OF THE DRAWING

The present invention may be more fully and easily understood when taken in conjunction with the accompanying drawing, in which:

FIG. 11A is a cross-sectional view of the Frank localizer conventionally known in the art;

FIG. 11B is a cross-sectional view of the Kopans locater conventionally known in the art;

FIG. 11C is a cross-sectional view of the Homer needle/wire localizer conventionally known in the art;

FIG. 11D is a cross-sectional view of the Sadowsky marking needle conventionally known in the art;

FIG. 3 is a cross-sectional view of the rod element of the present invention;

FIG. 4 is a cross sectional view of one embodiment of the present invention in the advanced position;

FIG. 5 is a cross-sectional view of one embodiment of the present invention in the engaged position;

DETAILED DESCRIPTION OF THE PREFERRED EMBODIMENT

The present invention is an adjustable biopsy localization device which, even in its simplest format, comprises only three elements: a cannula, a small tube for insertion into a body tissue or cavity, having a substantially cylindrical wall and an internal lumen; on open slot or side port in the tubular wall; and a pointed-tipped rod inserted into and passing through the lumen of the cannula, this rod being partially split along its length to provide a barb-like appendage which is extendable and retractable through the slot of the tubular wall. Preferred embodiments provide means for rotating the rod along its central longitudinal axis; and means for maintaining the rod in the cannula at a preselected alignment position appropriate for either extension of the barb-like appendage through the slot of the tubular wall (to engage and secure the device within the tissues) or to retract the barb-like appendage into the lumen of the cannula (for disengagement of the guide device). Preferred embodiments also provide means for advancing and withdrawing the pointed rod through the lumen of the cannula to either project the pointed tip of rod beyond the cannula or conceal it within the lumen.

The present invention provides a number of different major advantages to the user in comparison to wire/needle devices conventionally known. The present invention may be preassembled as a unit, sterilized, and prepackaged for use. The pointed tip of the rod is non-deflecting in comparison with the beveled syringe needle tip typically employed. The localization device may be advanced easily through the tissues, secured by engagement into the surrounding area, disengaged at will, and subsequently removed as often as desired. The device may be repositioned as often as is required to become localized at a specific target lesion or mass. In its engaged position, the device has firm bidirectional security and cannot accidently slip forward or backward in the tissue. Surgically, the cannula shaft is easy for the surgeon to follow; easily palpable; and can be approached from any direction. There is no need for additional wire thickening or wire reinforcement to avoid accidental breakage or inadvertent loss into the tissues. Once inserted at a localized site, the tissues may slide freely around the cannula and the patient may move freely without fear of changing the positioning of the rod tip relative to the target site. Finally, in the event that the target lesion is found to contain fluid matter, it is possible to remove the rod completely and utilize the cannula as a double port (end hole and open slot) aspiration device.

Figure 1:
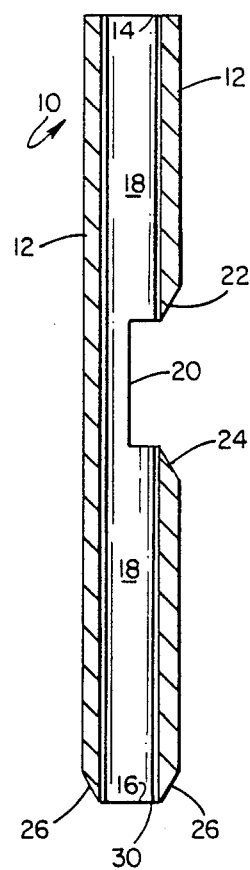
FIG. 1 is a cross-sectional view of the cannula comprising one element of the present invention.
Figure 2:
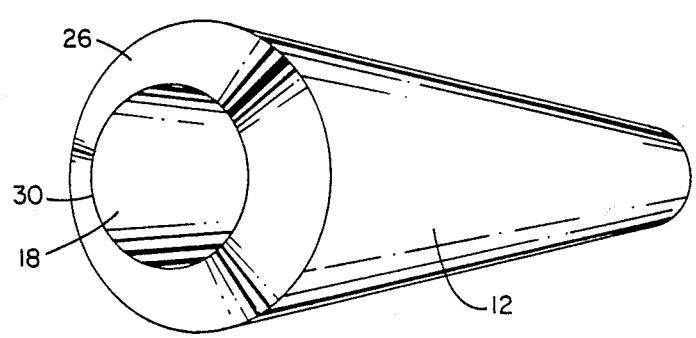
FIG. 2 is a perspective view of the distal end of the cannula illustrated in FIG. 1.

The simplest embodiment of the present invention is illustrated by FIGS. 1-5 which provide cross-sectional views of the present invention as individual elements and as an assembled unit. FIG. 1 shows a canula 10 having a substantially cylindrical tubular wall 12, a proximal end 14, a distal end 16, and an internal lumen 18. Along the length of the tubular wall 12, there is an open slot or side port 20 which preferably has beveled margins 22, 24 sloping inwardly towards the lumen 18. It is also preferred that the distal end 16 of the tubular wall 12 is beveled inwardly toward the center at the margin 26 and terminates as a straight edge 30 at right angles to the cannula as illustrated by FIG. 2.

The other essential element is illustrated in FIG. 3 as a rod 50 formed of a durable metal whose distal end is preferably configured as a conical-shaped tip 52 and whose proximal end is configured as a L-shaped rotation handle 54. The rod 50 comprises a thicker main shaft 56 which is partially split along its length to provide a thinner shaft pillar 58 and an extendable barb-like appendage 60 which flexes outwardly when unrestrained, but aligns along the central longitudinal axis of the rod 50 when placed under restraint.

The assembled, operational unit comprising the simplest embodiment of the present invention is illustrated by FIGS. 4 and 5 respectively. As seen in FIG. 4, the assembled unit is ready for insertion into the tissues of the subject at a preselected site of entry. The rod 50 has been inserted into and passed through the lumen 18 of the cannula 10 having an adjustable screw clamp 80 mounted thereon and the conical-shaped pointed tip 52 extends beyond the narrowed straight edges 30 of the distal end 16. The alignment of the rod 50 for purposes of insertion is crucial and should conform substantially to that relationship illustrated by FIG. 4 wherein the extendable appendage 60 is aligned within the lumen 18 of the cannula 10 such that the appendage 60 is in a restrain position and lies substantially parallel to the central longitudinal axis of the rod. Preferably the extendable appendage 60 is positioned within the lumen 18 to be remote from the slot 20 in the tubular wall 12. After insertion of the assembled device at the chosen site to the desired depth in the tissue, the rod 50 is rotated approximately 180° along its central longitudinal axis within the lumen 18 of the cannula 10 thus bringing the extendable appendage 60 into adjacent relationship with the open slot 20. The rod 50 is then pulled upwards through the lumen 18 of the cannula 10, preferably by pulling on the rotation handle 54. As the rod 50 recedes within the lumen 18, the appendage 60 enters into and extends through the open slot 20 into the surrounding tissue of the subject. This is the engaged position for the localization device and is illustrated by FIG. 5 in which the extended barb-like appendage 60 and the blunt cannula edge 30 secure and maintain the unit in the precise insertion site until disengaged. In the engaged mode, the site of insertion may be verified by radiological films without fear of accidentally moving or losing the localization device.

If the target lesion has not been reached, the secured guide device may be quickly and conveniently disengaged by advancing the rod forward through the lumen 18 of the cannula 10 until the original advanced position is again achieved wherein the pointed tip 52 of the rod 50 again extends beyond the straight edge 30 of the cannula. The act of advancing the rod 50 through the lumen 18 will cause a retraction of the barb-like appendage 60 into the lumen of the cannula. When the conical-shaped pointed tip 52 of the rod is fully advanced beyond the distal end 16 of the cannula 10, the entirety of the extendable appendage 60 will be again within the lumen of the cannula. Once in the advanced position, the rod 50 is preferably rotated approximately 180° using the rotation handle 54 until the initial insertion position illustrated by FIG. 4 is again reached. The localization device, as a unit, may then be withdrawn and reinserted at a different site as often as required.

The cannula is preferably made of needle tubing of variable diameter and length to meet specific requirements. Typically, a useful cannula is 10 cm long, has an outer diameter of about 0.035 inches and has a thin tubular wall providing an inner diameter of about 0.024 inches. It will be recognized that none of these dimensions are critical and that the user may prepare a cannula of any desired length; having any desired outer and inner diameters; and formed of any material which is suitable for use under surgical conditions. The rod to be inserted into and passed through the cannula is substantially a wire formed of stainless steel or other hard materials having a typical outer diameter of about 0.020 inches. The composition of the rod or wire should have sufficient tensile strength such that the proximal end may be configured to meet a variety of different shapes and needs; and will provide for rotation of the rod many times under a variety of torque conditions without twisting, bending, or breaking. Clearly, the dimensions of the rod in length and in diameter will vary with and conform to the inner diameter of the cannula. Accordingly, a wide variety of sizes may be prepared to meet specific uses and circumstances. Preferably, however, the tolerances between the diameter of the rod and the inner diameter of the cannula are very small such that there is very little space for the rod to vibrate, flex, or otherwise alter its position after insertion into the lumen of the cannula.

It should be noted also that the cannula edge 30 at the distal end 16 of the cannula is formed by an inward beveling of the tubular wall diameter which terminates as a straight edge at right angles to the annular lumen. This preferred format provides parallel circular edges with inwardly beveled margins which minimizes tearing and unnecessary injury to the tissues of the subject at the point of insertion. This is in contradistinction to the conventional uneven, beveled cutting edge of syringe needles which not only act as incision points but tend to deflect the tip of the needle off its intended course. With the present invention, it is noteworthy that the actual cutting edge function is performed by the preferably conical-shaped pointed tip of the rod rather than by the narrowed margins of the tubular wall at the distal end. The preferred, conical-shaped rod lip is non-deflecting substantially inflexible, and provides a smooth, sharp leading point while the device is being advanced but which is no longer in contact with the tissues of the patient once the localization device has been secured in the engaged position.

In the intended and expected mode of use, the novel biopsy guide device will be utilized in conjunction with standard radiographic films or fluoroscopy identifying the target lesion in at least two different views. The breast or other tissue may be held in a radiolucent compression device. Routine sterilization and local aesthesia are employed as is conventional in this technique. The site of insertion is preferably nicked and the localization device in the advanced position is inserted as a unit into the desired site at specific coordinates determined from the films or by fluoroscopy. The device is then advanced through the target region to a depth judged to be beyond it. The rod is then rotated and the extendable barb-like appendage engaged to secure the device in the manner earlier described. A right angle X-ray view of the rod shaft will demonstrate its relationship to the target lesion. If any adjustment is needed, the barb-like appendage is retracted by again advancing the rod within the lumen of the cannula to disengage the device; and then subsequently rotating the rod within the cannula to again achieve the original insertion position. The localization device may be then repositioned as necessary until the conical-shaped rod tip is within or close to the target lesion. The patient is then sent to the surgeon for biopsy with the device secured in the engaged position and the exact relationship of its tip relative to the target lesion documented on the final set of films. The cannula distal end and the extended appendage serve to guide the surgeon to the target lesion itself.

Figure 6:
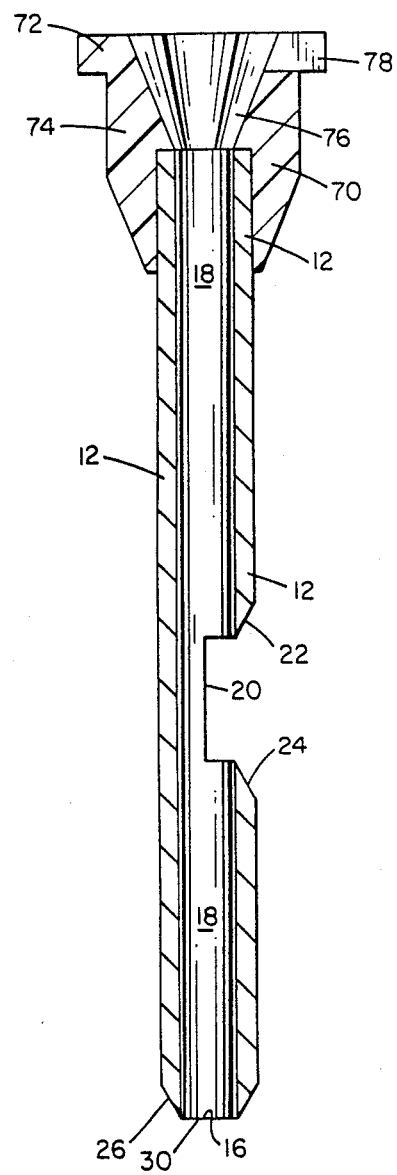
FIG. 6 is a cross-sectional view of the preferred cannula comprising part of the present invention.
Figure 7:
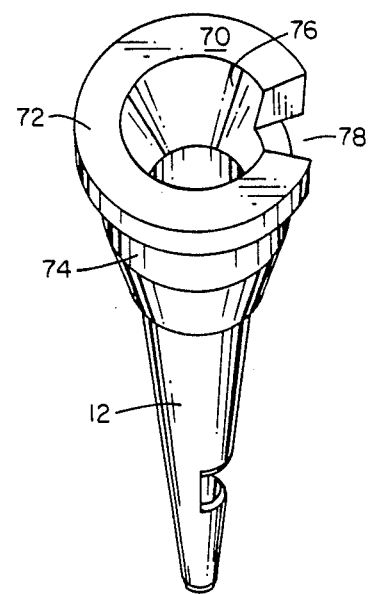
FIG. 7 is a perspective view of the hub disposed upon the cannula in the preferred embodiment of the present invention.

Preferred embodiments of the biopsy guide device are illustrated by FIGS. 6–10 respectively. The preferred cannula is illustrated by FIGS. 6 and 7 which include the cannula previously described in FIG. 1 in its entirety. In addition, however, at the proximal end 14 of the cannula 10, there is disposed a hub 70 comprising a substantially circular hub ledge 72 and a hub support 74. A central aperture or hole 76 exists along the central axis of the hub 70 which extends into and merges with the lumen 18 of the cannula 10. A notch 78 in the hub ledge 72 is positioned to be substantially in alignment with the open slot 20 in the tubular wall 12. The hub is preferably made of a resilient material such as plastic or metal and is preferably attached to the proximal end of the cannula to form an integral unit using conventional sealing techniques and compositions.

Figures 8, 9, 10:
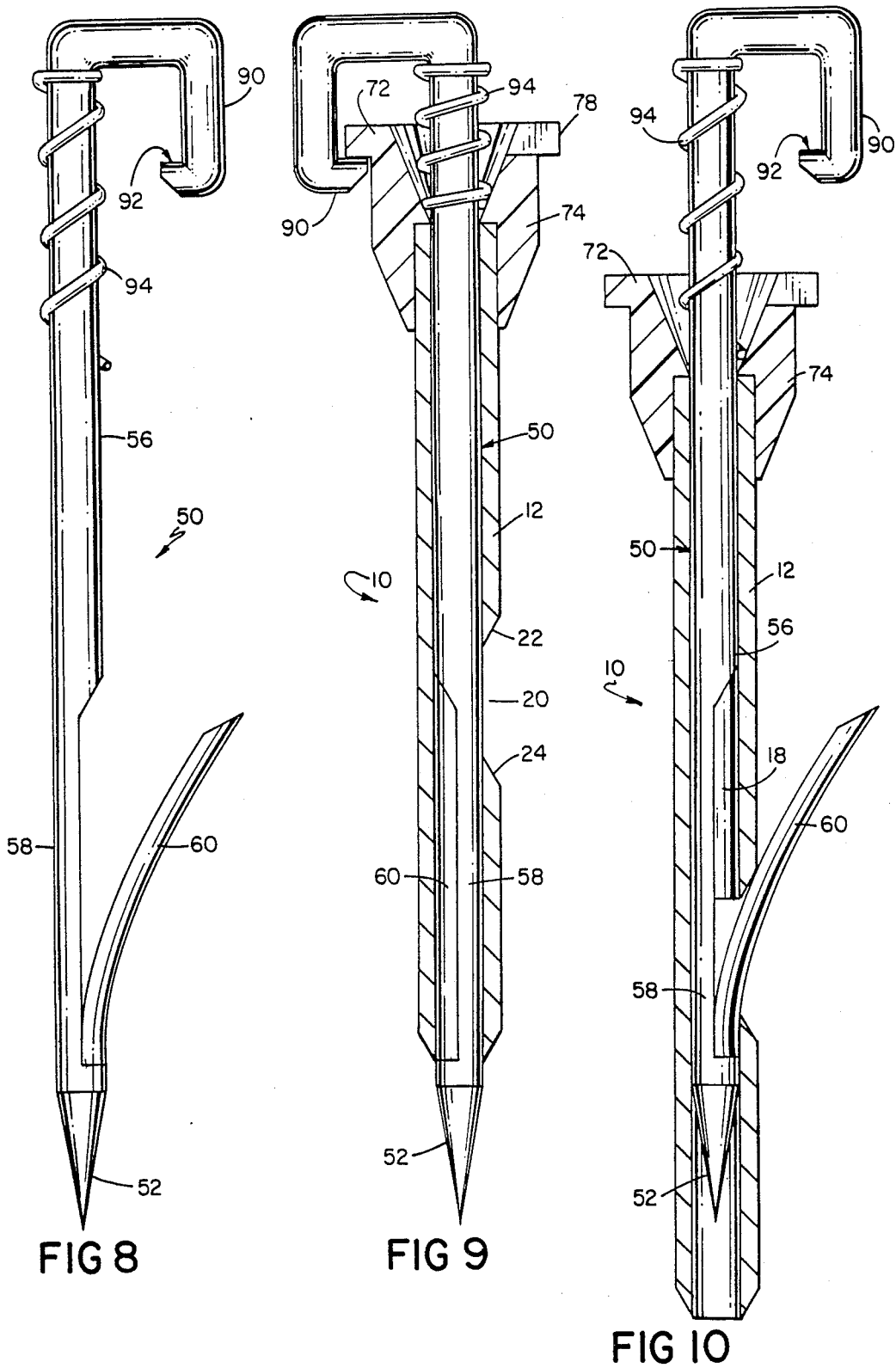
FIG. 8 is a cross-sectional view of the preferred rod element comprising the present invention.
FIG. 9 is a cross-sectional view of the preferred embodiment of the present invention in the advanced position.
FIG. 10 is a cross-sectional view of a preferred embodiment of the present invention in the engaged position.

The rod element is illustrated by FIG. 8 which reproduces substantially all the features of the rod previously described in FIG. 3 but whose proximal end has been lengthened and configured as a C-shaped crook 90. The end of the crook 90 appears as a retention lever 92. A coiled spring is threaded around the proximal end 14 of the rod 50 and is maintained in position by the hub 70 and the crook 90.

The preferred cannula and rod elements are assembled as a unit and usefully employed as illustrated by FIGS. 9 and 10 respectively, which correspond in function and use to the units described by FIGS. 4 and 5 previously. FIG. 9 shows the biopsy localization device in the advanced position suitable for insertion of the device at a preselected target site. The conical-shaped pointed tip 52 is advanced beyond the distal end 16 of the cannula 10. This advanced position is maintained by the engagement of the crook 90 with the hub ledge 72 substantially as shown. The coiled spring 94 has been concomitantly placed under compression force whose action maintains the crook 90 at the desired stance. After the device has been inserted to the desired depth within the tissue of the subject, the crook 90 is rotated around the hub 70 until it is aligned with the notch 78 in the hub ledge 72. The rotation of the crook 90 around the hub 70 to the notch 78 also causes a positional rotation of the extendable appendage 60 within the lumen 18 such that the appendage is placed in adjacent relationship to the open slot 20. The coiled spring 94 releases its compression force thereby causing the crook 90 to pass through the notch 78 in the hub ledge 72 and extend for a short distance above the notch substantially as illustrated in FIG. 10. Concomitantly, as the rod recedes through the lumen 18, the appendage 60 enters and passes through the open slot 90 and extends outward as a harb-like projection into the tissues of the subject and arrests further receding movement of the rod. The extension of the appendage 60 through the open slot 20 secures the localization device and places the unit in the engaged mode. To disengage the guide device for any reason, the crook 90 is advanced forward through the notch 78 of the hub 70 thereby causing the coiled spring to again be placed again under compression force and concomitantly causing retraction of the appendage 60 back into the lumen 18 of the cannula 10. The crook is then preferably rotated to engage the hub ledge 72 and again assume the position illustrated by FIG. 9, the advanced position. The guide device may then be reoriented, removed, and reinserted if desired or as necessary.

The present invention is not to be restricted in form nor limited in scope except by the claims appended hereto.

What I claim is:

1. An adjustable biopsy localization device comprising:
   a single cannula having a substantially tubular wall and an internal lumen;
   an open slot in said tubular wall;
   a pointed rod inserted into said lumen of said cannula, said rod being advanceable, retractable and rotatable within said lumen; and
   an extendable and retractable appendage means disposed on said rod, said appendage means being rotatably alignable with said slot and being extendable for anchoring said device at a target biopsy site in a subject's body and being retractable through said slot in said tubular wall for enabling removal and possible relocation of said device.

2. The adjustable biopsy localization device as recited in claim 1 further comprising means for advancing, retracting and rotating said rod within said lumen of said cannula.

3. The adjustable biopsy localization device as recited in claim 1 further comprising:
   one end of said rod being configured as a crook;
   a hub disposed upon said tubular wall at on end of said cannula;
   a coiled spring mounted on said rod; and
   a notch in said hub.

4. The adjustable biopsy localization device as recited in claim 1 wherein one end of said tubular wall terminates as a straight edge.

5. The adjustable biopsy localization device as recited in claim 1 wherein said rod point is substantially conical-shaped.

6. The adjustable biopsy localization device as recited in claim 1 wherein an adjustable screw-clamp is mounted on said cannula.

7. The adjustable biopsy localization device as recited in claim 1 wherein:
   said pointed rod is partially split along its length; and
   said extendable and retractable appendage is disposed upon said partially split length of said rod.

* * * * *